(12) United States Patent
Nakamura et al.

(10) Patent No.: US 9,124,026 B2
(45) Date of Patent: Sep. 1, 2015

(54) CABLE ASSEMBLY, ELECTRONIC CIRCUIT MODULE, AND IMAGING APPARATUS

(75) Inventors: Mikio Nakamura, Tokyo (JP); Hiroshi Suzushima, Nagano (JP); Fukashi Yoshizawa, Tokyo (JP); Hideharu Miyahara, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 457 days.

(21) Appl. No.: 12/859,987

(22) Filed: Aug. 20, 2010

(65) Prior Publication Data
US 2011/0042140 A1  Feb. 24, 2011

(30) Foreign Application Priority Data
Aug. 20, 2009 (JP) ................................. 2009-190835

(51) Int. Cl.
*H01R 13/6593* (2011.01)
*H01R 12/62* (2011.01)
*A61B 1/00* (2006.01)
*H01R 9/05* (2006.01)
*H01R 13/02* (2006.01)

(52) U.S. Cl.
CPC ............ *H01R 12/62* (2013.01); *A61B 1/00114* (2013.01); *H01R 9/0515* (2013.01); *H01R 13/025* (2013.01)

(58) Field of Classification Search
USPC ................ 174/75 C, 78, 88 C, 117 F, 117 FF
See application file for complete search history.

(56) References Cited

U.S. PATENT DOCUMENTS

| 5,206,462 A * | 4/1993 | Iura et al. ................... 174/117 F |
| 5,710,393 A * | 1/1998 | Smith et al. ................. 174/74 R |
| 6,943,452 B2 * | 9/2005 | Bertin et al. ................. 257/774 |
| 7,628,647 B2 * | 12/2009 | Semba et al. ................ 439/579 |

FOREIGN PATENT DOCUMENTS

| JP | 2003-143728 A | 5/2003 |
| JP | 3863583 | 10/2006 |
| JP | 2008-258053 A | 10/2008 |

OTHER PUBLICATIONS

Japanese Office Action dated Nov. 19, 2013 from related Japanese Application No. 2009-190835, together with an English language translation.

* cited by examiner

*Primary Examiner* — Chau N Nguyen
(74) *Attorney, Agent, or Firm* — Scully, Scott, Murphy & Presser, PC (57) ABSTRACT

A cable assembly includes a plurality of cables; and a cable fixing member which has a facing surface to be oppositely arranged, in connecting each of the cables to a member as a connection target, with respect to a connection surface of the connection target member and fixes a distal end part of each of the cables in a state where an axial direction of the distal end part of each of the cables is arranged along the facing surface, wherein a side surface of a core wire of each of the cables is exposed at a predetermined first position on the facing surface of the cable fixing member and a first connection part which connects the core wire of each of the cables to the connection target member is formed at the first exposed part.

6 Claims, 9 Drawing Sheets

FIG.17

CABLE ASSEMBLY, ELECTRONIC CIRCUIT MODULE, AND IMAGING APPARATUS

CROSS-REFERENCE TO RELATED APPLICATIONS

This application is based upon and claims the benefit of priority from Japanese Patent Application No. 2009-190835, filed on Aug. 20, 2009, the entire contents of which are incorporated herein by reference.

BACKGROUND OF THE INVENTION

1. Field of the Invention

The present invention relates to a cable assembly, an electronic circuit module, and an imaging apparatus.

2. Description of the Related Art

Conventionally, an endoscope which is inserted into an inside of a subject and performs an observation of a test site has been known and widely used in the medical field and the like. In a circuit at a distal end part of the endoscope, a cable assembly which enables collectively connecting a plurality of cables is used and downsizing thereof is realized by reducing a length of a hard part which functions as a connection terminal part. For example, a cable assembly in which a plurality of cables are fixed by using an array block which forms a hard part is known (see Japanese Patent No. 3863583, for example). Japanese Patent No. 3863583 discloses a configuration of the cable assembly which connects an end surface of the array block exposing a distal end surface of each cable to a plane part of a circuit board provided with an electrode.

SUMMARY OF THE INVENTION

According to an aspect of the present invention, a cable assembly includes a plurality of cables; and a cable fixing member which has a facing surface to be oppositely arranged, in connecting each of the cables to a member as a connection target, with respect to a connection surface of the connection target member and fixes a distal end part of each of the cables in a state where an axial direction of the distal end part of each of the cables is arranged along the facing surface, wherein a side surface of a core wire of each of the cables is exposed at a predetermined first position on the facing surface of the cable fixing member and a first connection part which connects the core wire of each of the cables to the connection target member is formed at the first exposed part.

According to another aspect of the present invention, an electronic circuit module includes a cable assembly including a plurality of cables and a cable fixing member which has a facing surface to be oppositely arranged, in connecting each of the cables to a member as a connection target, with respect to a connection surface of the connection target member and fixes a distal end part of each of the cables in a state where an axial direction of the distal end part of each of the cables is arranged along the facing surface, wherein a side surface of a core wire of each of the cables is exposed at a predetermined position on the facing surface of the cable fixing member and a connection part which connects the core wire of each of the cables to the connection target member is formed at the exposed part; and the member provided with a cable connecting electrode which is formed on the connection surface and connected to the connection part of each of the cables, wherein the connection part and the cable connecting electrode are connected.

According to still another aspect of the present invention, an imaging apparatus includes a cable assembly including a plurality of cables and a cable fixing member which has a facing surface to be oppositely arranged, in connecting each of the cables to a member as a connection target, with respect to a connection surface of the connection target member and fixes a distal end part of each of the cables in a state where an axial direction of the distal end part of each of the cables is arranged along the facing surface, wherein a side surface of a core wire of each of the cables is exposed at a predetermined position on the facing surface of the cable fixing member and a connection part which connects the core wire of each of the cables to the connection target member is formed at the exposed part; the member provided with a cable connecting electrode which is formed on the connection surface and connected to the connection part of each of the cables; and an imaging device mounted on the connection surface, wherein one of respective connection parts of the cables is electrically connected to the imaging device.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of the present invention will be explained in detail below with reference to the accompanying drawings. Here, the present invention will not be limited to the embodiments. Throughout the description of the drawings, a common part will be provided with a common reference character.

Figure 1:
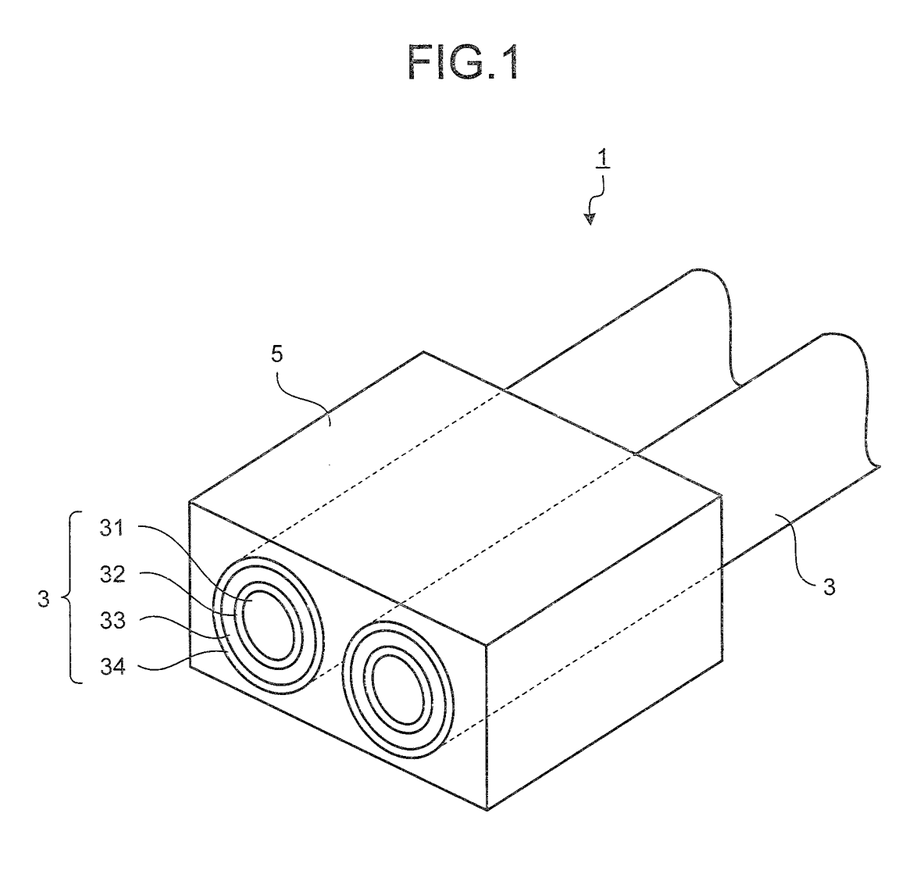
FIG. 1 is a perspective view illustrating a configuration example of a cable assembly according to an embodiment.
Figure 2:
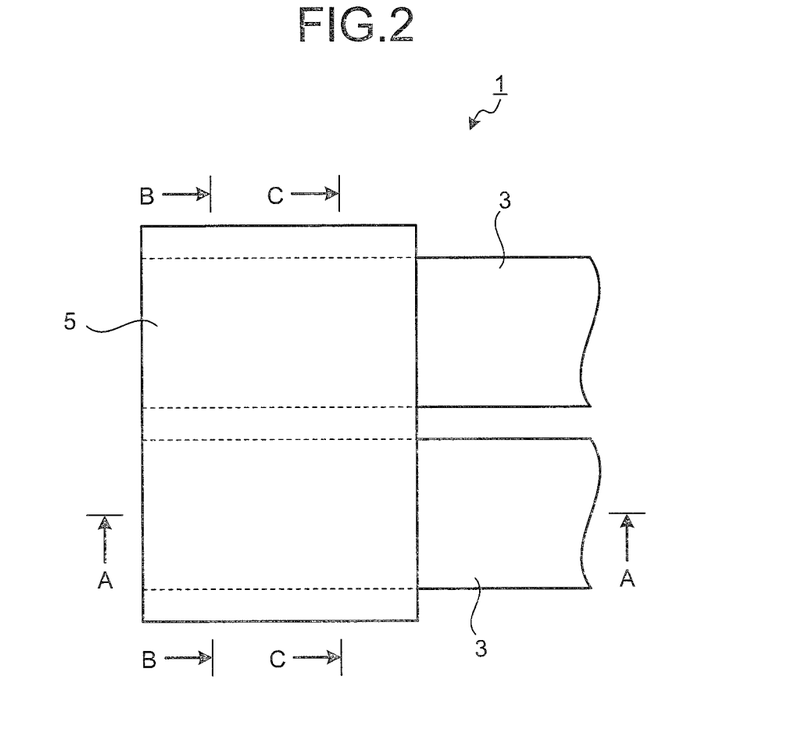
FIG. 2 is a plane view of the cable assembly according to the embodiment.
Figure 3:
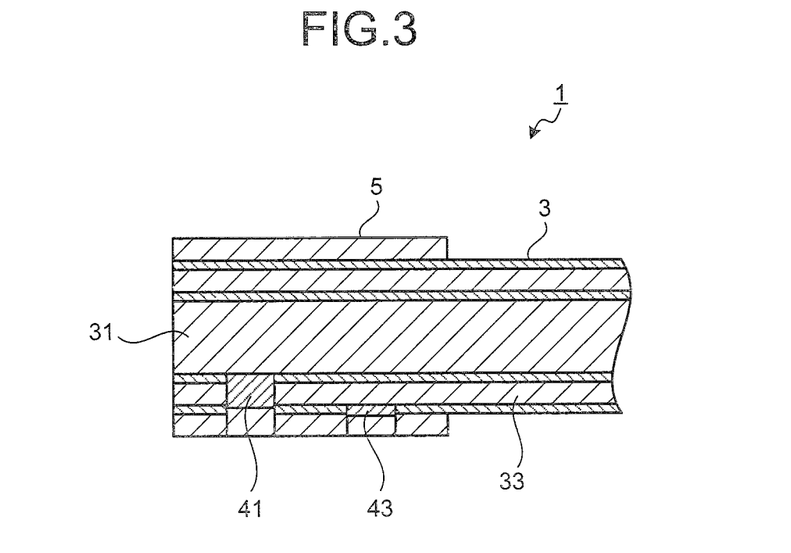
FIG. 3 is a cross-sectional view along line A-A in FIG. 2.
Figure 4:
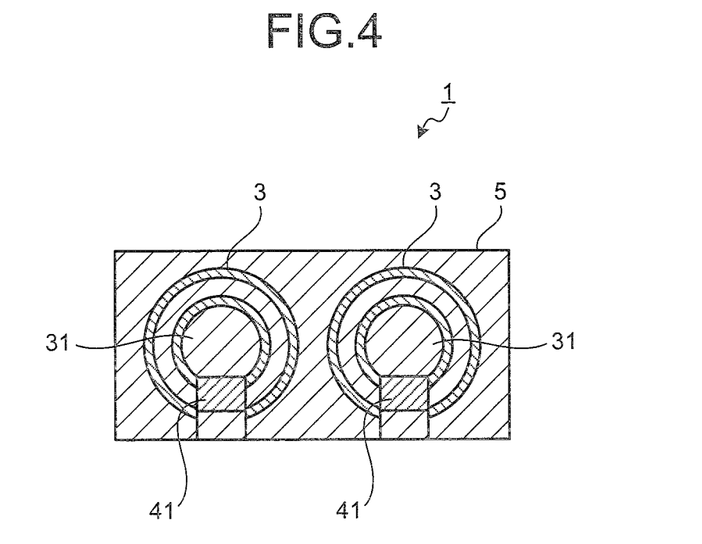
FIG. 4 is a cross-sectional view along line B-B in FIG. 2.
Figure 5:
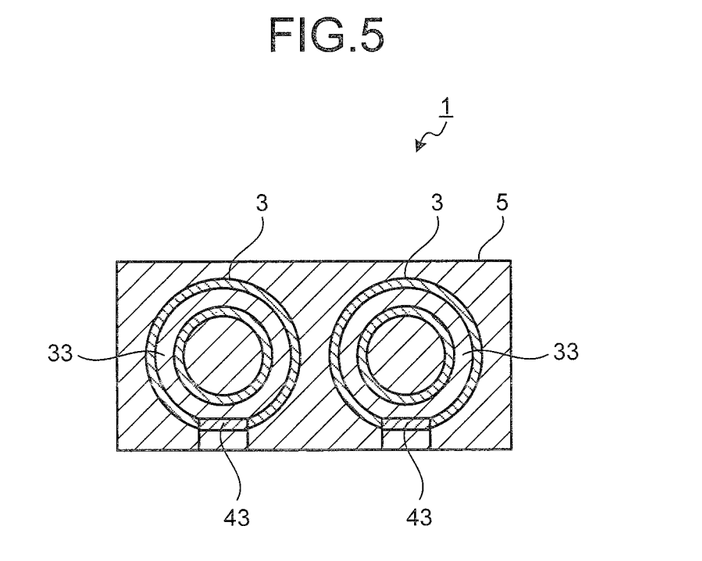
FIG. 5 is a cross-sectional view along line C-C in FIG. 2.

FIG. 1 is a perspective view illustrating a configuration example of a cable assembly 1 according to an embodiment. FIG. 2 is a plane view of the cable assembly 1. FIG. 3 is a cross-sectional view along line A-A in FIG. 2, FIG. 4 is a cross-sectional view along line B-B in FIG. 2, and FIG. 5 is a cross-sectional view along line C-C in FIG. 2. While a cable assembly bundling two cables 3 is illustrated in FIGS. 1 to 5, the number of cables constituting the cable assembly can be selected arbitrarily depending on a requirement.

As shown in each of FIGS. 1 to 5, the cable assembly 1 is constituted by two cables 3 and a cable fixing member 5 which has a block shape and fixes the cables 3.

The cables 3 are, for example, coaxial cables having the same radius and each is configured such that an outer conductor (a shielded wire) 33 is formed in an outer circumference of a center conductor (a core wire) 31 via an inner insulating body 32 and an outer insulating body 34 is provided in an outer circumference of the outer conductor 33 as shown in FIG. 1.

The cable fixing member 5 is formed of a resin and the like. In the embodiment, a bottom surface of the cable fixing member 5 is configured to be a facing surface and a distal end part of each cable 3 is fixed in a state where an axial direction of the distal end part of each cable 3 is arranged along the facing surface.

On the facing surface (the bottom surface) of the cable fixing member 5, a part of a side surface of the center conductor 31 of each cable 3 is exposed at a predetermined connection position of the center conductor at a lower side of the cable 3 as shown in FIGS. 3 and 4. Then, a connection part 41 which electrically connects the center conductor 31 of each cable 3 to an outside is formed at this exposed part. Besides, on the facing surface of the cable fixing member 5, a part of a side surface of the outer conductor 33 of each cable 3 is exposed at a predetermined connection position of the outer conductor at a lower side of the cable 3, this position being different from the connection position of the center conductor, as shown in FIGS. 3 and 5. Then, a connection part 43 which electrically connects the outer conductor 33 of each cable 3 to an outside is formed at this exposed part.

In manufacturing the cable assembly 1, the distal end part of each cable 3 is fixed by the cable fixing member 5 in a state where the axial direction of the distal end part of each cable 3 is arranged along the facing surface. After that, the side surface of the center conductor 31 of each cable 3 is exposed at the connection position of the center conductor on the facing surface of the cable fixing member 5 and the connection part 41 is formed via metal film plating on the exposed part. In addition, the side surface of the outer conductor 33 of each cable 3 is exposed at the connection position of the outer conductor on the facing surface of the cable fixing member 5 and the connection part 43 is formed via the metal film plating on the exposed part.

According to the embodiment as described, respective distal end parts of the cables 3 are fixed, in a state where respective axial directions of the distal end parts of the plurality of cables 3 are arranged along the facing surface, by the cable fixing member 5 which has the facing surface to be oppositely arranged with respect to a connection surface of a member as a connection target. Then, the side surface of the center conductor 31 of each cable 3 is exposed at the predetermined connection position of the center conductor on the facing surface of the cable fixing member 5 and the connection part 41 which connects the center conductor 31 of each cable 3 to the connection target member is formed. In addition, the side surface of the outer conductor 33 of each cable 3 is exposed at the predetermined connection position of the outer conductor on the facing surface of the cable fixing member 5 and the connection part 43 which connects the outer conductor 33 of each cable 3 to the connection target member is formed. Therefore, even in a case where the cable assembly 1 cannot be orthogonally arranged with respect to the connection surface of the connection target member, the cables can be connected while maintaining a small body.

The cable assembly 1 is applied to an electronic circuit module and connected to a connection target member, for example, a substrate via the connection parts 41 and 43. Here, the substrate may be a wiring substrate on which a wiring pattern is formed and may be a substrate which interiorly implements an electronic circuit.

Figure 6:
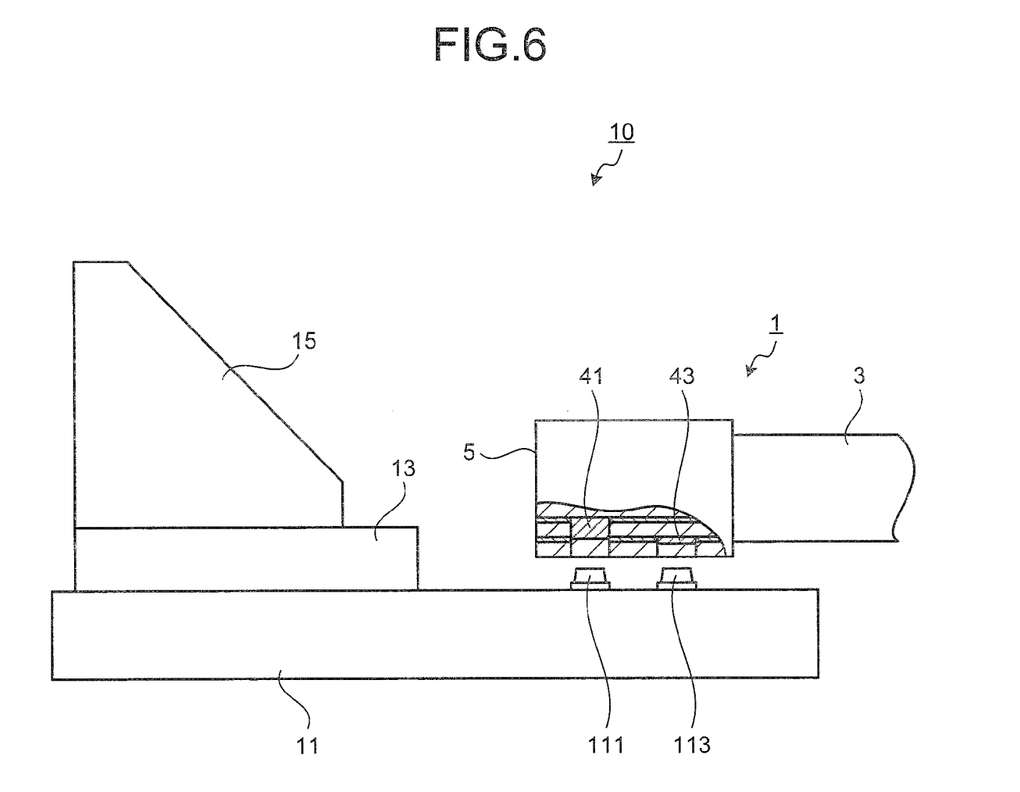
FIG. 6 is an explanatory view of a configuration of an imaging apparatus to which the cable assembly according to the embodiment is applied.

Besides, the cable assembly 1 can be applied to an imaging apparatus which is provided at a distal end part of an endoscope, for example. FIG. 6 is an explanatory view of a configuration of an imaging apparatus 10 to which the cable assembly 1 according to the embodiment is applied. In FIG. 6, a part of the cable assembly 1 is cut off and a cross section of the part is illustrated.

The imaging apparatus 10 shown in FIG. 6 is provided with a circuit board 11, an imaging device 13 mounted on a main surface as a connection surface of the circuit board 11, and a prism 15 placed on an upper surface of the imaging device 13. On the connection surface (main surface) of the circuit board 11, cable connecting electrodes (protruding electrodes) 111 and 113 which are respectively connected to the connection parts 41 and 43 formed on the facing surface of the cable fixing member 5 of the cable assembly 1 are formed respectively at predetermined positions avoiding an area for mounting the imaging device 13, electronic parts not shown, and the like. More specifically, the cable connecting electrode 111 which is connected to the connection part 41 formed by exposing the center conductor 31 of each cable 3 and the cable connecting electrode 113 which is connected to the connection part 43 formed by exposing the outer conductor 33 of each cable 3 are formed by being arranged in two lines.

Here, the connection parts 41 and 43 formed on the facing surface of the cable fixing member 5 in the cable assembly 1 and the cable connecting electrodes 111 and 113 formed on the connection surface of the circuit board 11 are respectively formed at mutually-connectable positions on the facing surface and the connection surface when the facing surface of the cable fixing member 5 is oppositely arranged with respect to the connection surface of the circuit board 11.

Then, the facing surface of the cable fixing member 5 and the connection surface of the circuit board 11 are oppositely arranged in connecting the cable assembly 1 and the circuit board 11, and the connection parts 41 and 43 on the facing surface and the cable connecting electrodes 111 and 113 are connected respectively by a solder and the like, for example.

Here, while the connection target member is exemplified as a substrate in the embodiment described above, the present invention can be similarly applied to a case of connecting the cable assembly to an electronic part or an electronic circuit module.

Figure 7:
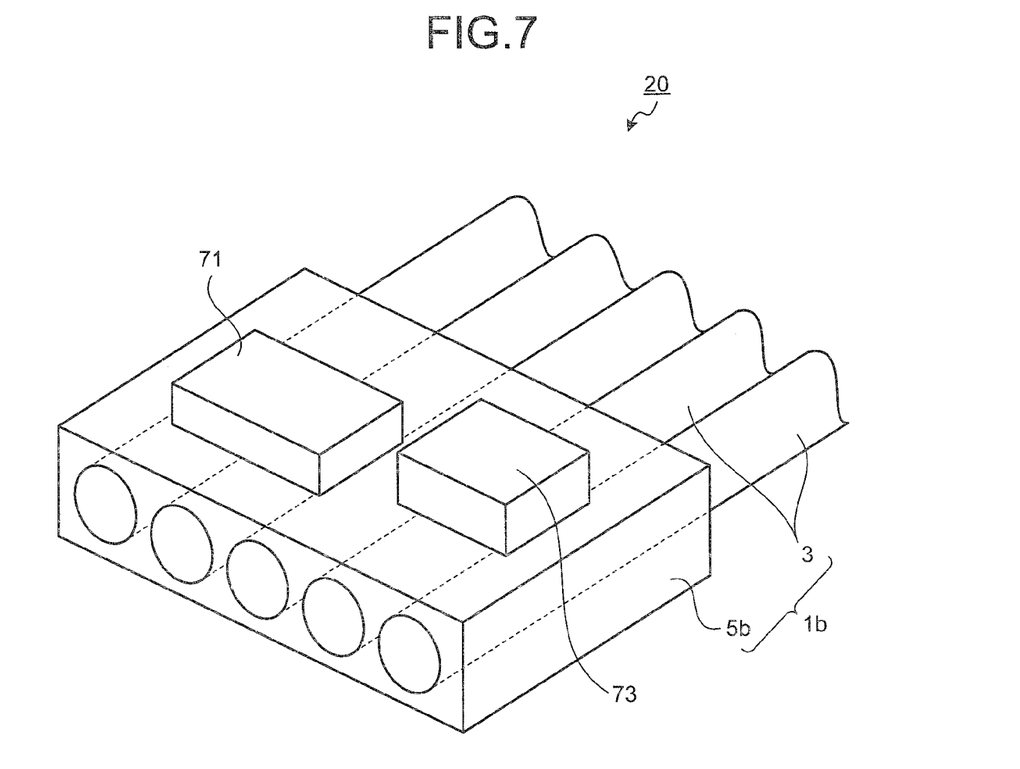
FIG. 7 is a perspective view of an electronic circuit module to which a cable assembly according to a first modification is applied.

Moreover, while the case of treating the bottom surface of the cable fixing member 5 as the facing surface is explained in the embodiment described above, an upper surface side may be treated as the facing surface and the connection parts may be formed. FIG. 7 is a perspective view of an electronic circuit module 20 to which a cable assembly 1b according to a first modification is applied. Here in FIG. 7, the cable assembly 1b in which five cables 3 are bundled and fixed by a cable fixing member 5b is illustrated.

In the cable assembly 1b according to the first modification, an upper surface of the cable fixing member 5b is treated as the facing surface and connection target members 71 and 73 which are electronic parts such as a capacitor placed on the upper surface are connected to the cables 3. Here, the two members 71 and 73 placed on the cable fixing member 5b are configured by being provided with cable connecting electrodes which are not shown and formed on the bottom surfaces of the two members 71 and 73 each as the connection surface, respectively.

In manufacturing the electronic circuit module 20, side surfaces of the center conductor and the outer conductor of each cable 3 are arbitrarily exposed at predetermined connection positions of the center conductor and the outer conductor respectively on the facing surface (upper surface) of the cable fixing member 5b and respective connection parts are formed. Then, the facing surface (upper surface) of the cable fixing member 5b is made to face the connection surfaces of the connection target members 71 and 73 and the connection parts on the facing surface and cable connecting electrodes formed on the connection surfaces of the members 71 and 73 are connected by a solder and the like, for example.

According to the first modification, electronic parts and the like can be mounted on the upper surface of the cable fixing member 5b. For example when the configuration of the electronic circuit module 20 according to the first modification is applied to the imaging apparatus 10 shown in FIG. 6, electronic parts can be mounted by utilizing a space on the cable fixing member 5b. Thus, an area for mounting an imaging device, electronic parts, and the like of a circuit board can be narrowed as well as a high density of a device can be realized, so that a device can further be downsized.

In the embodiment described above, the axial direction of the distal end part of each cable 3 is arranged in line along the facing surface and fixed by the cable fixing member 5. In contrast, when each of the bottom surface and the upper surface of the cable fixing member is configured to be the facing surface as described in the first modification example, cables can be arranged on two stages. Specifically, cables to be connected to a member located at the bottom surface side may be arranged at the bottom surface side on a lower stage and cables to be connected to a member located at the upper surface side may be arranged at the upper surface side on the upper stage.

Figure 8:
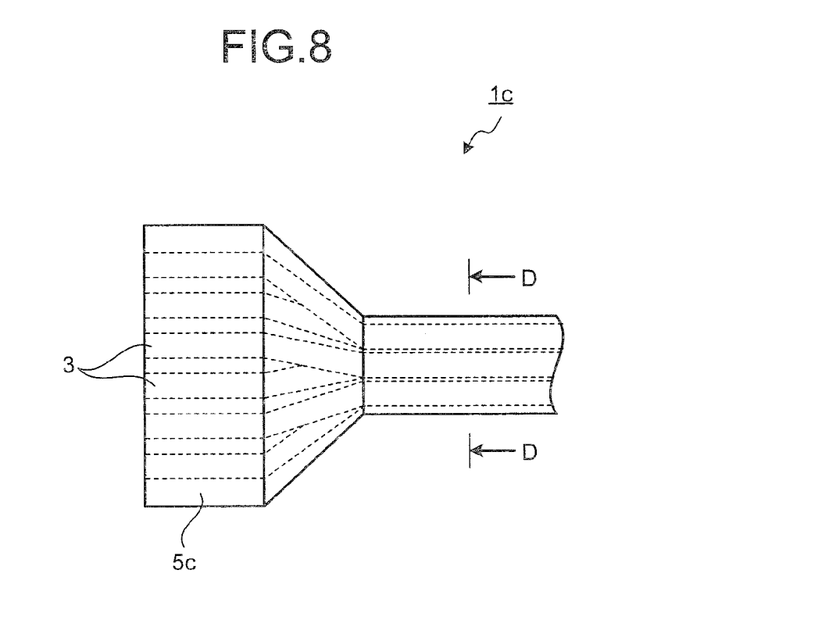
FIG. 8 is a plane view of a cable assembly according to a second modification.
Figure 9:
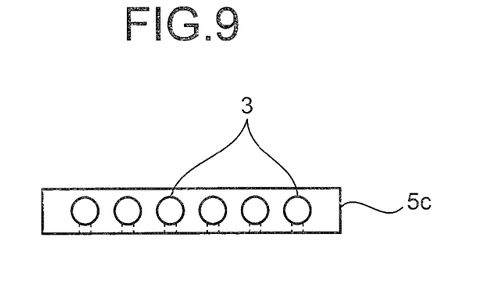
FIG. 9 is a front view of the cable assembly according to the second modification.
Figure 10:
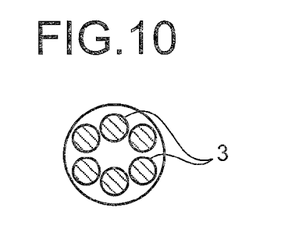
FIG. 10 is a cross-sectional view along line D-D in FIG. 8.

Besides, in manufacturing a cable assembly by bundling a lot of cables, the cables can be bundled sterically except for the distal end parts of the cables. FIG. 8 is a plane view of a cable assembly 1c according to a second modification and FIG. 9 is a front view of the cable assembly 1c. FIG. 10 is a cross-sectional view along line D-D in FIG. 8. FIGS. 8 to 10 illustrate the cable assembly 1c in which six cables 3 are bundled and fixed by a cable fixing member 5c.

As shown in FIGS. 8 and 9, the cable fixing member 5c fixes the distal end part of each cable 3 in a state where the axial direction of the distal end part of each cable 3 is arranged along, for example, a bottom surface as the facing surface. Here, respective side surfaces of the center conductor and the outer conductor of each cable 3 are exposed as shown by the broken line in FIG. 9 at a predetermined connection position of the center conductor and at a predetermined connection position of the outer conductor on the bottom surface which is the facing surface of the cable fixing member 5c and respective connection parts not shown are formed. As shown in FIGS. 8 and 10, the cables 3 are bundled sterically except for the distal end parts thereof.

While the embodiment described above is configured such that the connection parts 41 and 43 are formed by exposing the side surfaces of the center conductor 31 and the outer conductor 33 of each cable 3 on the facing surface of the cable fixing member 5 respectively, the present invention is not limited thereto.

Figure 11:
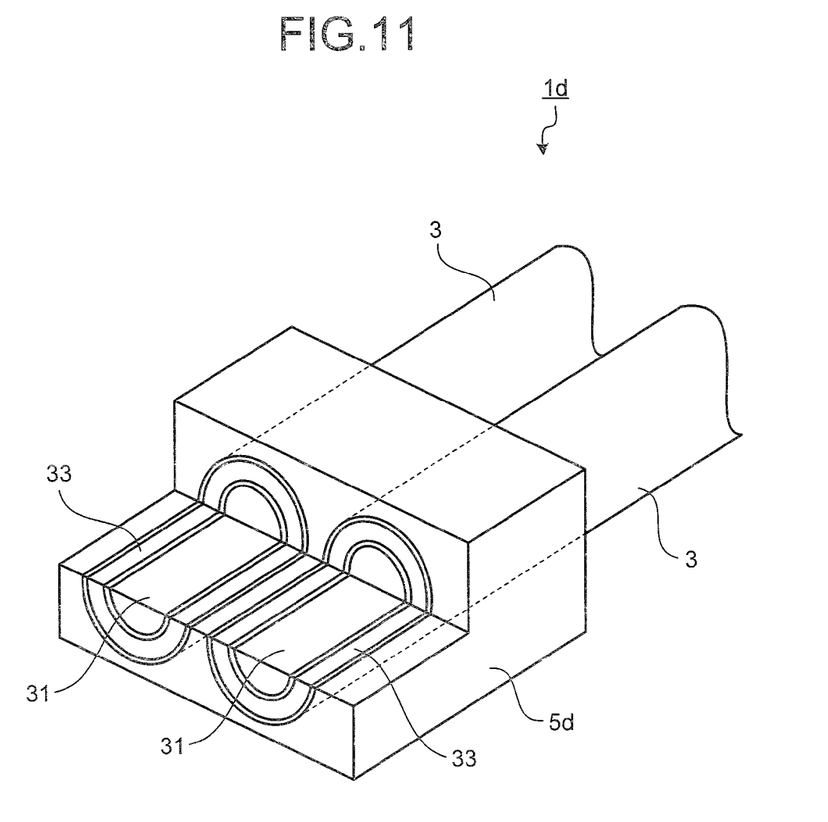
FIG. 11 is a perspective view illustrating a configuration example of a cable assembly according to a third modification.
Figure 12:
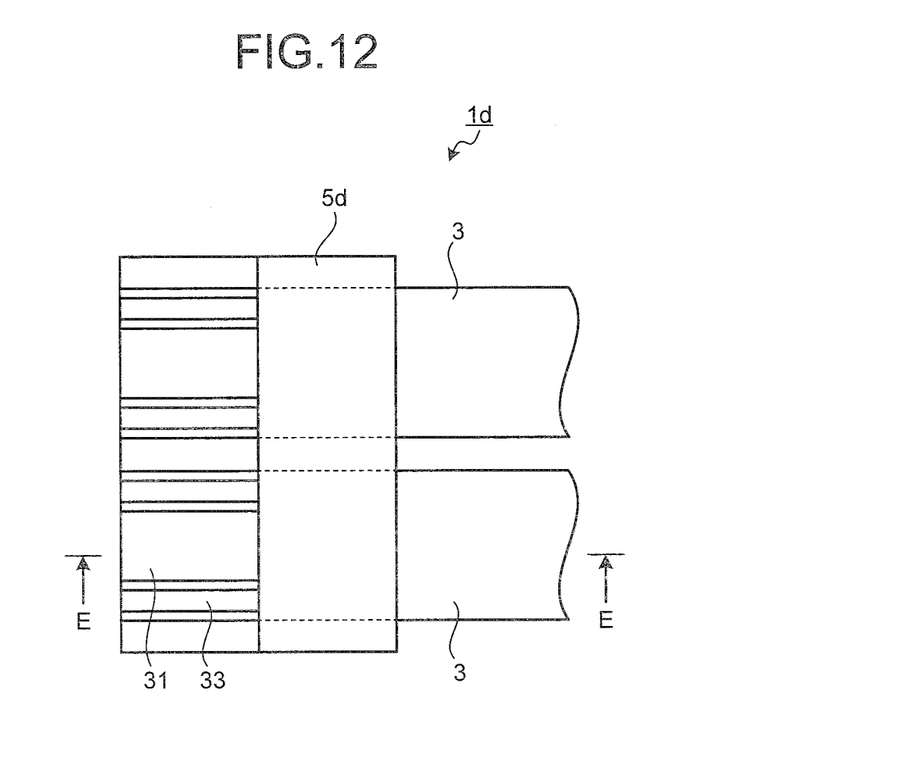
FIG. 12 is a plane view of the cable assembly according to the third modification.
Figure 13:
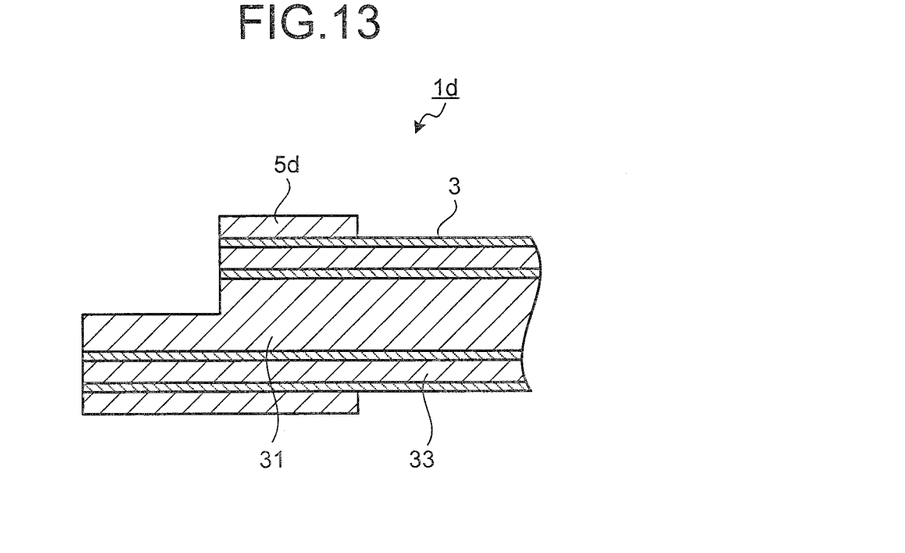
FIG. 13 is a cross-sectional view along line E-E in FIG. 12.
Figure 14:
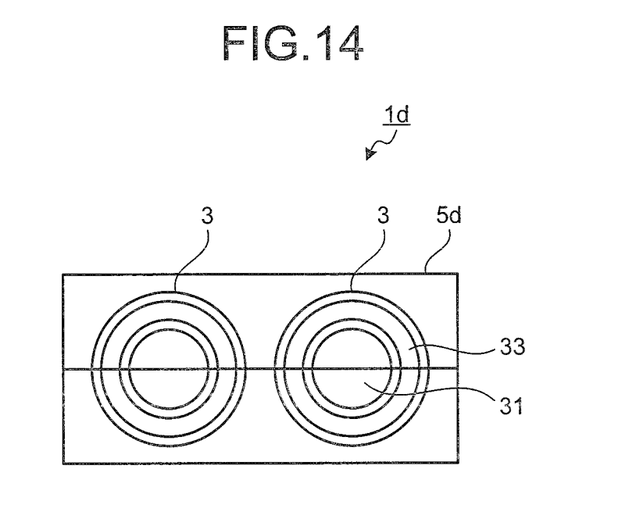
FIG. 14 is a front view of the cable assembly according to the third modification.

FIG. 11 is a perspective view illustrating a configuration example of a cable assembly 1d according to a third modification. FIG. 12 is a plane view of the cable assembly 1d and FIG. 13 is a cross-sectional view along line E-E in FIG. 12. FIG. 14 is a front view of the cable assembly 1d. As shown in each of FIGS. 11 to 14, the third modification is configured such that the center conductor 31 and the outer conductor 33 are exposed by buffing a facing surface of a cable fixing member 5d and providing a step.

According to the third modification, the cable fixing member 5d can be processed at a time to expose the center conductor 31 and the outer conductor 33 of each cable 3. Thus, the connection parts can be formed easily and a cost reduction can be realized. In this case, as for a cable connecting electrode formed in a connection target member, a cable connecting electrode for the center conductor 31 and a cable connecting electrode for the outer conductor 33 are formed in such a way as to be arranged alternately along a radial direction of the cable 3. Here, the center conductor 31 and the outer conductor 33 of each cable 3 may be connected to the connection target member by forming an electrode part having a shape of fitting in the step part of the cable assembly 1d on the connection surface of the connection target member and fitting the electrode part in the step part.

Figure 15:
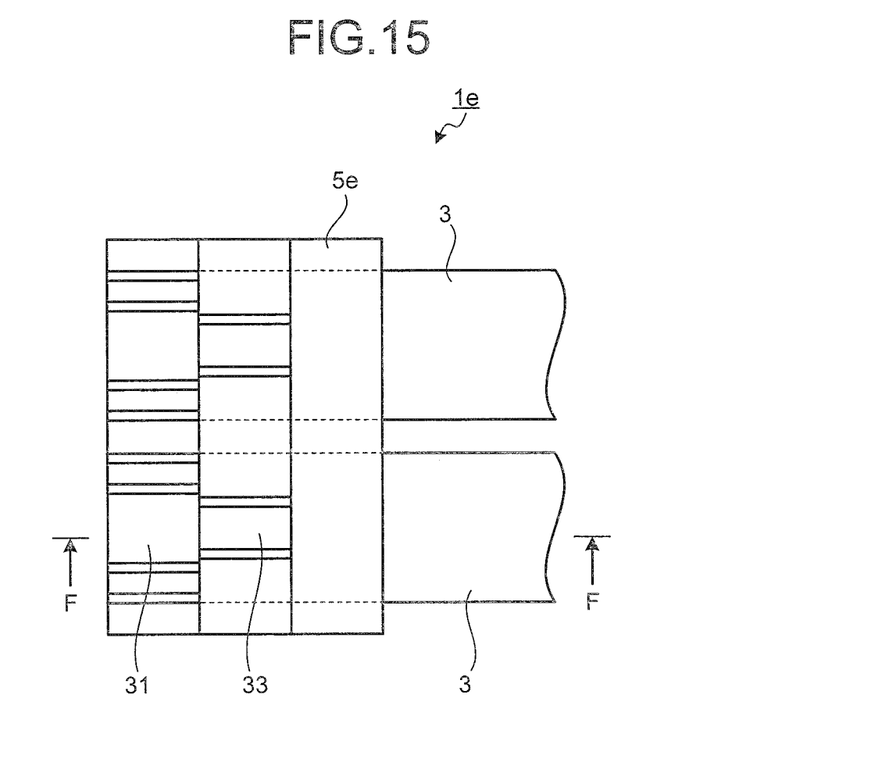
FIG. 15 is a plane view of a cable assembly according to a fourth modification.
Figure 16:
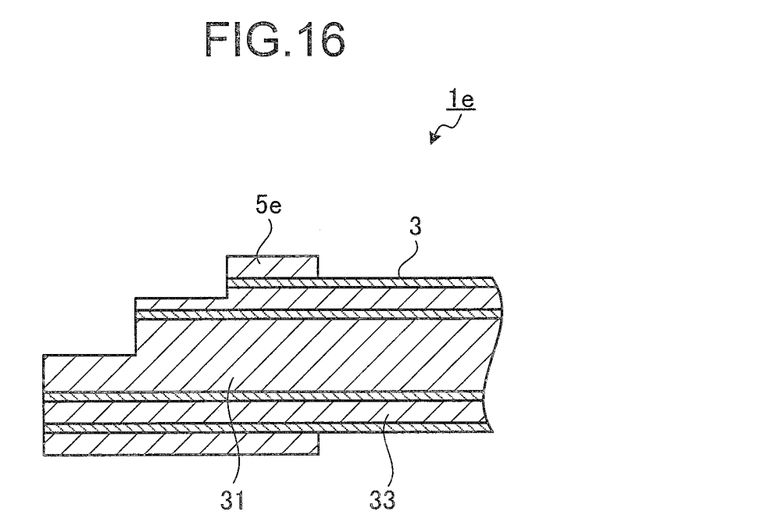
FIG. 16 is a cross-sectional view along line F-F in FIG. 15.
Figure 17:
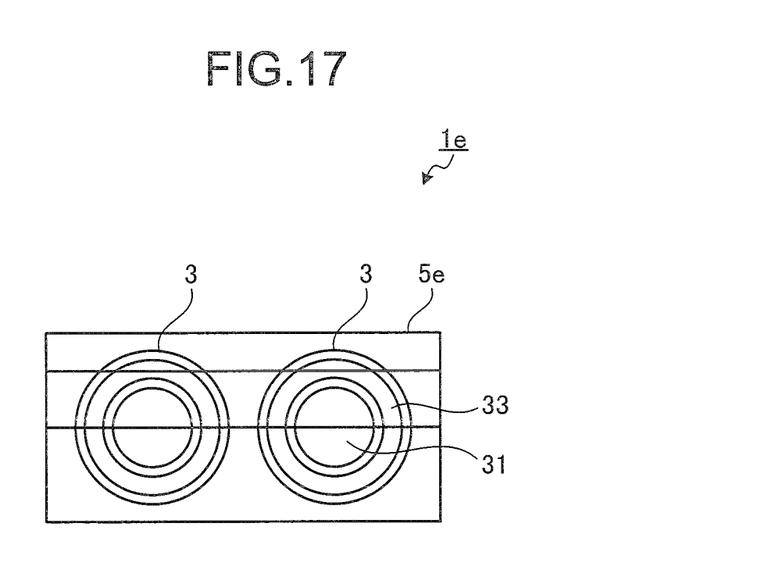
FIG. 17 is a front view of the cable assembly according to the fourth modification.

In addition, FIG. 15 is a plane view of a cable assembly 1e according to a fourth modification and FIG. 16 is a cross-sectional view along line F-F in FIG. 15. FIG. 17 is a front view of the cable assembly 1e. As shown in each of FIGS. 15 to 17, the configuration may be such that two steps are provided on a facing surface of a cable fixing member 5e and the center conductor 31 and the outer conductor 33 are exposed in stages. The connection parts can be formed easily and a cost reduction can be realized similarly in the fourth modification. Besides, the center conductor 31 and the outer conductor 33 of each cable 3 may be connected to the connection target member by forming an electrode part having a shape of fitting in the step part of the cable assembly 1e on the connection surface of the connection target member and fitting the electrode part in the step part.

According to the fourth modification, the outer conductor 33 of each cable 3 can be exposed in the first step of the cable fixing member 5e. In this case, cable connecting electrodes with the outer conductors 33 of respective cables 3, among cable connecting electrodes formed in the connection target member, may be formed as a common electrode instead of respective protruding electrodes.

In the cable assembly, the electronic circuit module, and the imaging apparatus according to the present invention, respective distal end parts of a plurality of cables 3 are fixed by a cable fixing member having a facing surface which is oppositely arranged with respect to a connection surface of a member as a connection target in a state where respective axial directions of the distal end parts of the plurality of cables 3 are arranged along the facing surface. Then, a side surface of a core wire of each cable is exposed at a predetermined position on the facing surface of the cable fixing member and a connection part for connecting the core wire of each cable to the connection target member is formed. Therefore, even in a case where the cable assembly cannot be orthogonally arranged with respect to the connection surface of the connection target member, the cables can be connected while maintaining a small body.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A cable assembly that is connected to a first member to which a cable connecting electrode is formed, comprising:
   a plurality of cables; and
   a cable fixing member which has a facing surface to be oppositely arranged with respect to a connection surface of the first member and fixes a distal end part of each of the cables in a state where an axial direction of the distal end part of each of the cables is arranged along the facing surface, wherein,
   a side surface of a core wire of a portion of the distal end part of the each of the cables fixed by the cable fixing member is exposed at a first exposed part only at a lower side of the cables facing the cable connecting electrode, and a first connection part which connects the core wire of each of the cables to the first member is formed at the first exposed part;
   wherein
   an outer conductor is formed in an outer circumference of the core wire of each of the cables, and
   a side surface of the outer conductor of each of the cables is exposed at a second exposed part, the second exposed part being at a predetermined position different from where the first connection part is formed on the facing surface, and a second connection part which connects the outer conductor of each of the cables to the first member is additionally formed at the second exposed part.

2. The cable assembly according to claim 1, wherein the facing surface is provided with two steps by buffing the cable fixing member together with the cables to expose the center conductor and the outer conductor in stages.

3. An electronic circuit module, comprising:
   a first member with a connection surface to which first and second cable connecting electrodes are formed; and
   a cable assembly that is connected to the first member, including
      a plurality of cables, and
      a cable fixing member which has a facing surface to be oppositely arranged with respect to the connection surface of the first member and fixes a distal end part of each of the cables in a state where an axial direction of the distal end part of each of the cables is arranged along the facing surface, wherein
   a side surface of a core wire of a portion of the distal end part of the each of the cables fixed by the cable fixing member is exposed at a first exposed part only at a lower side of the cables facing the first cable connecting electrode, and a first connection part which connects the core wire of each of the cables to the first member is formed at the first exposed part,
   an outer conductor is formed in an outer circumference of the core wire of each of the cables, and
   a side surface of the outer conductor of each of the cables is exposed at a second exposed part, the second exposed part being at a predetermined position different from where the first connection part is formed on the facing surface, and a second connection part which connects the outer conductor of each of the cables to the first member is additionally formed at the second exposed part;
   wherein the first connection part and the first cable connecting electrode are connected and the second connection part and the second cable connecting electrode are connected.

4. The electronic circuit module according to claim 3, wherein the first and second connection parts and the first and second cable connecting electrodes are formed at positions respectively on the facing surface and on the connection surface so that the first and second connection parts and the respective first and second cable connecting electrodes can be connected with each other when the facing surface is oppositely arranged with respect to the connection surface.

5. The electronic circuit module according to claim 3, wherein the first member to be connected to the first and second connection parts includes separate members.

6. An imaging apparatus, comprising:
   a first member with a connection surface to which first and second cable connecting electrodes are formed;
   a cable assembly that is connected to the first member, including
      a plurality of cables, and
      a cable fixing member which has a facing surface to be oppositely arranged with respect to the connection surface of the first member and fixes a distal end part of each of the cables in a state where an axial direction of the distal end part of each of the cables is arranged along the facing surface, wherein
   a side surface of a core wire of each of a portion of the distal end part of the each of the cables fixed by the cable fixing member is exposed at a first exposed part only at a lower side of the cables facing the first cable connecting electrode, and a first connection part which connects the core wire of each of the cables to the first member is formed at the first exposed part;
   an outer conductor is formed in an outer circumference of the core wire of each of the cables,
   a side surface of the outer conductor of each of the cables is exposed at a second exposed part, the second exposed part being at a predetermined position different from where the first connection part is formed on the facing surface, and a second connection part which connects the outer conductor of each of the cables to the first member is additionally formed at the second exposed part; and
   an imaging device mounted on the connection surface, wherein each of the first and second connection parts of the cables is electrically connected to the imaging device.

* * * * *